United States Patent
Benning et al.

(10) Patent No.: US 11,278,194 B2
(45) Date of Patent: *Mar. 22, 2022

(54) ENDOSCOPIC SYSTEM FOR ENHANCED VISUALIZATION

(71) Applicant: Boston Scientific Scimed, Inc., Maple Grove, MN (US)

(72) Inventors: Christopher A. Benning, Hopkinton, MA (US); Paul Daniel Aquilino, Walpole, MA (US)

(73) Assignee: Boston Scientific Scimed. Inc., Maple Grove, MN (US)

( * ) Notice: Subject to any disclaimer, the term of this patent is extended or adjusted under 35 U.S.C. 154(b) by 1299 days.

This patent is subject to a terminal disclaimer.

(21) Appl. No.: 14/972,499

(22) Filed: Dec. 17, 2015

(65) Prior Publication Data

US 2016/0100749 A1  Apr. 14, 2016
US 2020/0170490 A9  Jun. 4, 2020

Related U.S. Application Data

(63) Continuation of application No. 13/155,632, filed on Jun. 8, 2011, now Pat. No. 9,277,855.

(Continued)

(51) Int. Cl.
*A61B 1/06* (2006.01)
*A61B 1/07* (2006.01)

(52) U.S. Cl.
CPC .......... *A61B 1/0607* (2013.01); *A61B 1/0638* (2013.01); *A61B 1/0676* (2013.01); *A61B 1/0684* (2013.01); *A61B 1/07* (2013.01)

(58) Field of Classification Search
CPC .... A61B 1/04; A61B 1/05; A61B 1/06; A61B 1/07; A61B 1/00163; A61B 1/00165;
(Continued)

(56) References Cited

U.S. PATENT DOCUMENTS 8,292,805 B2 * 10/2012 Vayser .................. A61B 90/30
600/249
8,771,176 B2 * 7/2014 Hendriks ................. A61B 1/06
600/167

(Continued)

FOREIGN PATENT DOCUMENTS

EP   2 163 185 A1   3/2010

OTHER PUBLICATIONS

PCT International Search Report and Written Opinion issued in corresponding PCT International Application No. PCT/US2011/039590, dated Sep. 23, 2011 (13 pages).

*Primary Examiner* — Ryan N Henderson
(74) *Attorney, Agent, or Firm* — Bookoff McAndrews, PLLC

(57) ABSTRACT

A medical device, configured for insertion into a body, may include an elongate member extending from a proximal end to a distal end, where the distal end may be configured to be positioned inside the body. The medical device may also include an imaging device positioned at the distal end. The medical device may further include a plurality of light sources positioned at the distal end, wherein a characteristic of light delivered through a first light source may be controlled independent of the characteristic of light delivered through a second light source.

16 Claims, 5 Drawing Sheets

Related U.S. Application Data

(60) Provisional application No. 61/372,114, filed on Aug. 10, 2010.

(58) Field of Classification Search
CPC .............. A61B 1/00167; A61B 1/0017; A61B 1/00172; A61B 1/00174; A61B 1/00177; A61B 1/00179; A61B 1/00181; A61B 1/00183; A61B 1/00186; A61B 1/00188; A61B 1/0019
See application file for complete search history.

(56) References Cited

U.S. PATENT DOCUMENTS

| | | | |
|---|---|---|---|
| 8,795,157 B1* | 8/2014 | Yaron | A61B 1/31 600/111 |
| 2003/0028078 A1* | 2/2003 | Glukhovsky | A61B 1/0676 600/109 |
| 2003/0117491 A1* | 6/2003 | Avni | A61B 1/045 348/77 |
| 2003/0191368 A1 | 10/2003 | Wang et al. | |
| 2004/0105264 A1 | 6/2004 | Spero | |
| 2004/0186351 A1 | 9/2004 | Imaizumi et al. | |
| 2005/0124858 A1* | 6/2005 | Matsuzawa | A61B 1/0607 600/176 |
| 2005/0213092 A1 | 9/2005 | MacKinnon et al. | |
| 2005/0215911 A1* | 9/2005 | Alfano | A61B 1/041 600/476 |
| 2005/0219552 A1 | 10/2005 | Ackerman et al. | |
| 2005/0228231 A1 | 10/2005 | MacKinnon et al. | |
| 2005/0234302 A1 | 10/2005 | MacKinnon et al. | |
| 2006/0036131 A1* | 2/2006 | Glukhovsky | A61B 1/0638 600/160 |
| 2006/0069314 A1 | 3/2006 | Farr | |
| 2006/0120084 A1 | 6/2006 | Sueoka | |
| 2006/0149129 A1* | 7/2006 | Watts | A61B 1/0676 600/113 |
| 2006/0184039 A1* | 8/2006 | Avni | H04N 5/3696 600/476 |
| 2007/0059989 A1* | 3/2007 | Kura | A61B 1/04 439/685 |
| 2007/0088193 A1 | 4/2007 | Omori et al. | |
| 2007/0140582 A1 | 6/2007 | Chen et al. | |
| 2007/0225560 A1* | 9/2007 | Avni | A61B 1/0684 600/118 |
| 2008/0071144 A1* | 3/2008 | Fein | A61B 1/07 600/178 |
| 2008/0146877 A1 | 6/2008 | Matsuzawa et al. | |
| 2008/0158343 A1 | 7/2008 | Schechterman et al. | |
| 2008/0170846 A1* | 7/2008 | Wang | A61B 1/041 396/182 |
| 2008/0183043 A1* | 7/2008 | Spinnler | H04N 5/2256 600/178 |
| 2008/0239070 A1 | 10/2008 | Westwick et al. | |
| 2008/0249368 A1 | 10/2008 | Takei | |
| 2008/0287742 A1* | 11/2008 | St. George | A61B 1/00009 600/160 |
| 2009/0080184 A1 | 3/2009 | Kobilke | |
| 2009/0149713 A1* | 6/2009 | Niida | G02B 23/2484 600/167 |
| 2009/0177033 A1* | 7/2009 | Hendriks | A61B 1/0019 600/109 |
| 2009/0225333 A1 | 9/2009 | Bendall et al. | |
| 2009/0247881 A1 | 10/2009 | Maeda et al. | |
| 2009/0281389 A1* | 11/2009 | Iddan | A61B 1/041 600/167 |
| 2009/0303319 A1* | 12/2009 | Sato | A61B 34/73 348/65 |
| 2009/0306474 A1* | 12/2009 | Wilson | A61B 1/00006 600/109 |
| 2009/0306478 A1 | 12/2009 | Mizuyoshi | |
| 2009/0316116 A1* | 12/2009 | Melville | A61B 1/07 353/31 |
| 2010/0004513 A1 | 1/2010 | MacKinnon et al. | |
| 2010/0220179 A1* | 9/2010 | Wang | H04N 5/2354 348/68 |
| 2010/0220180 A1* | 9/2010 | Lee | A61B 5/073 348/74 |
| 2010/0272318 A1* | 10/2010 | Cabiri | A61B 5/7264 382/106 |
| 2011/0032350 A1* | 2/2011 | Kikuchi | G01N 21/251 348/135 |
| 2011/0112376 A1* | 5/2011 | Vayser | A61M 1/741 600/249 |
| 2011/0184243 A1* | 7/2011 | Wright | A61B 1/0676 600/180 |
| 2011/0205552 A1 | 8/2011 | Bendall et al. | |
| 2011/0208004 A1 | 8/2011 | Feingold et al. | |
| 2011/0218398 A1* | 9/2011 | Tamura | A61B 1/041 600/109 |
| 2012/0002394 A1 | 1/2012 | Todd et al. | |
| 2012/0059254 A1 | 3/2012 | Lifan et al. | |
| 2012/0092678 A1 | 4/2012 | Babayoff | |
| 2012/0262560 A1* | 10/2012 | Nisani | A61B 1/041 348/68 |
| 2013/0012794 A1* | 1/2013 | Zeng | A61B 1/063 600/328 |
| 2013/0020485 A1 | 1/2013 | Jung et al. | |
| 2013/0070985 A1 | 3/2013 | Babayoff | |
| 2013/0243284 A1 | 9/2013 | Babayoff | |
| 2015/0373288 A1* | 12/2015 | Wang | H04N 5/217 348/242 |

* cited by examiner

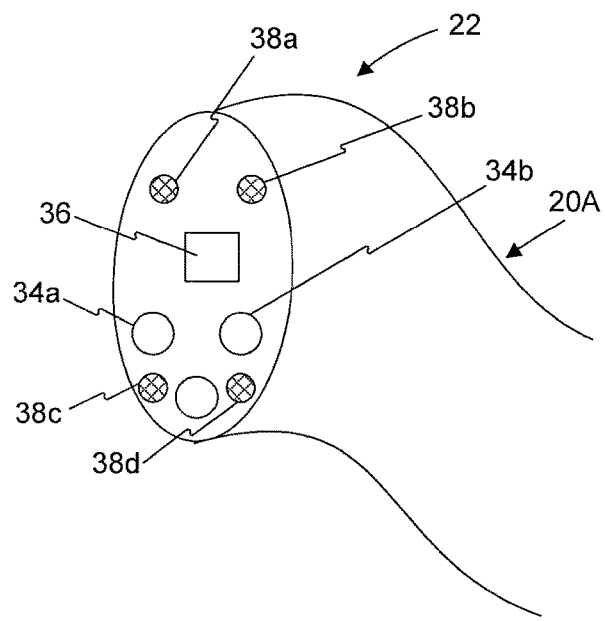 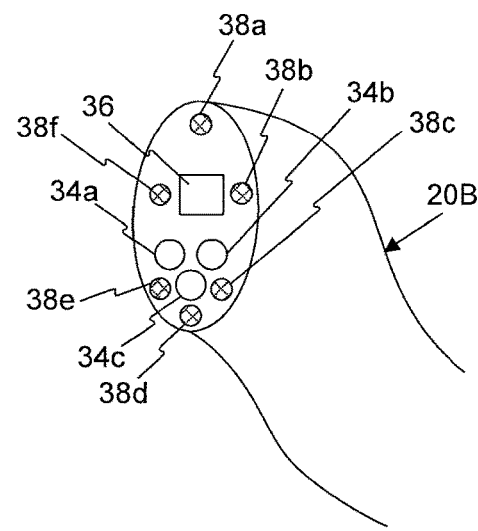
Fig. 4A      Fig. 4B
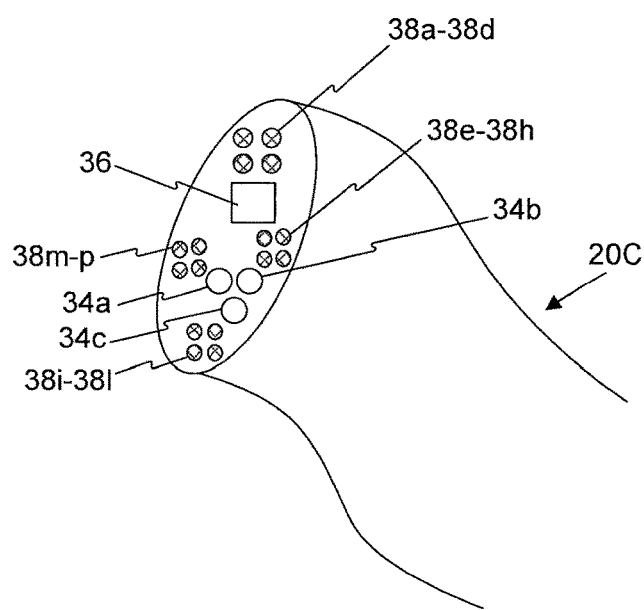
Fig. 4C

ENDOSCOPIC SYSTEM FOR ENHANCED VISUALIZATION

CROSS-REFERENCE TO RELATED APPLICATIONS

This application is a continuation of U.S. Nonprovisional patent application Ser. No. 13/155,632, filed on Jun. 8, 2011, which claims the benefit of priority under 35 U.S.C. § 119(e) to U.S. Provisional Patent Application No. 61/372,114, filed on Aug. 10, 2010, the entireties of each of which are incorporated herein by reference.

FIELD OF THE INVENTION

Embodiments of the present invention relate to an endoscopic system. In particular, exemplary embodiments of the present invention relate to endoscopes for enhanced visualization. Embodiments of the present invention also cover methods of using such devices.

BACKGROUND OF THE INVENTION

An endoscope is a flexible instrument introduced into the body for diagnostic or therapeutic purposes. Typically, these devices are inserted into the body through an opening (a natural opening or an incision), and are delivered to a work site inside the body through a body channel, such as, for example, the esophagus. Imaging devices incorporated in the endoscope allows a surgeon to see the work site from outside the body and remotely operate the endoscope to perform a desired diagnostic/therapeutic procedure at the work site. There are many different types of endoscopes in use today and embodiments of the current disclosure may be applied with any of these different types of endoscopes. In general, embodiments of the current disclosure may be applicable with any type of medical device that can be inserted into a body, and that allows a surgeon outside the body to visualize a region inside the body. For the sake of brevity, however, the novel aspects of the current disclosure will be described with reference to an endoscope.

In a typical application, a distal end of an endoscope may be inserted into the body through an opening in the body. This opening may be a natural anatomic opening, such as, for example, the mouth, rectum, vagina, etc., or an incision made on the body. The endoscope may be pushed into the body such that the distal end of the endoscope proceeds from the point of insertion to a region of interest (work site) within the body by traversing a body channel. The endoscope may include one or more lumens extending longitudinally from the proximal end to the distal end of the endoscope. These lumens may deliver various diagnostic/treatment devices to the work site to assist in the performance of the intended procedure at the work site.

Among others, these lumens may include an illumination lumen that includes an illumination source to illuminate a field of view at the work site, and an imaging lumen that includes an imaging device to capture an image of the work site and deliver the image outside the body. A diffusing lens may be used to attempt to project light evenly over the entire visualization field through the illumination lumen. Due to the differences in proximities, and other light reflecting characteristics of different locations within the field of view of the work site (such as, for example, differences in reflectivity of muscle and tissue), these different locations may appear to be illuminated differently. For instance, some of these locations may appear to be oversaturated with light while other locations may appear to be insufficiently illuminated. This variation in illumination may make visualization of the work site difficult, and may therefore be undesirable. An endoscope with a diffusing lens may, however, be limited to providing uniform light across the entire field of view. Additionally, with small bore endoscopes, the cost of implementing a diffusing lens for even distribution of light may be high. While this cost may be less of an issue with reusable endoscopes where the cost can be amortized due to repeated usage, this cost may be prohibitively high in the case of disposable endoscopes. The current disclosure is directed to systems and methods configured to enable clear visualization of a field of view within the body from outside the body.

SUMMARY OF THE INVENTION

An embodiment of the invention includes a medical device configured for insertion into a body. The medical device may include an elongate member extending from a proximal end to a distal end, where the distal end may be configured to be positioned inside the body. The medical device may also include an imaging device positioned at the distal end. The medical device may further include a plurality of light sources positioned at the distal end, wherein a characteristic of light delivered through a first light source may be controlled independent of the characteristic of light delivered through a second light source.

Various embodiments of the invention may include one or more of the following aspects: the plurality of light sources may include a plurality of fiber optic cables that terminate at the distal end; the plurality of light sources may include at least one LED; each of the plurality of light sources may be positioned at different locations at the distal end; the plurality of light sources may be configured to be illuminated by a common illumination source positioned outside the body; the characteristic of light may include at least one of an intensity, a wavelength, a polarization, a frequency, or a phase of light; the medical device may also include an illumination control system that is configured to vary the characteristic of light directed through the first light source independent of the characteristic of light directed through the second light source; the illumination control system may include controls that enable a user to manually vary the characteristic of light directed through the first light source independent of the characteristic of light directed through the second light source; the illumination control system may include an algorithm configured to automatically vary the characteristic of light directed through the first light source independent of the characteristic of light directed through the second light source; the algorithm may automatically vary the characteristic of light directed through the first light source independent of the characteristic of light directed through the second light source based on an illumination of an image captured by the imaging device; the medical device may also include an illumination control system that is configured to vary the characteristic of light based on input from one or more light sensors; and the medical device may be an endoscope.

An embodiment of the invention may also include a method of using a medical device. The method may include inserting a distal end of the medical device into a body. The medical device may extend from the distal end to a proximal end, and may include at least an imaging device and a plurality of light sources positioned at the distal end. The method may also include positioning the distal end proximate a work site within the body, and activating the imaging device to receive an image of the work site outside the body. The method may further include adjusting a characteristic of light directed through one of the light sources independent of the characteristic of light directed through other of the light sources based on the received image.

Various embodiments of the invention may include one or more of the following aspects: adjusting the characteristic of light may include varying an intensity of light directed through one of the light sources independent of the intensity of light directed through the other of the light sources; adjusting the characteristic of light may include manually adjusting the characteristic of light directed through one of the light sources independent of the characteristic of light directed through the other of the light sources; adjusting the characteristic of light may include automatically adjusting the characteristic of light directed through one of the light sources independent of the characteristic of light directed through the other of the light sources based on an illumination of the received image; and the characteristic of light may include at least one of an intensity, a wavelength, a polarization, a frequency, or a phase of light.

An embodiment of the invention may further include an endoscope. The endoscope may include an elongate body extending from a proximal end to a distal end, and an imaging device positioned at the distal end. The imaging device may be configured to direct an image of a work site proximate the distal end to a viewing device positioned proximate the proximal end. The endoscope may also include a plurality of light sources positioned at the distal end. The plurality of light sources may be configured to illuminate the work site. The endoscope may also include an illumination control system configured to vary a characteristic of light directed through one of the light sources independent of the characteristic of light directed through other of the light sources based on an illumination of the image on the viewing device.

Various embodiments of the invention may include one or more of the following aspects: the characteristic of light may include at least one of an intensity, a wavelength, a polarization, a frequency, or a phase of light; the plurality of light sources may include at least three light sources and the illumination control system may be configured to vary a characteristic of light directed through each one of the three light sources independent of the characteristic of light directed through the other two light sources; the illumination control system may be configured to automatically vary a characteristic of light directed through one of the light sources independent of the characteristic of light directed through the other of the light sources based on the illumination of the image; the plurality of light sources may include a plurality of fiber optic cables that terminate at the distal end, the plurality of light sources may be configured to be illuminated by a common illumination source positioned proximate the proximal end of the elongate body.

BRIEF DESCRIPTION OF THE DRAWINGS

The accompanying drawings, which are incorporated in and constitute a part of this specification, illustrate embodiments of the invention and together with the description, serve to explain the principles of the invention.

FIGS. 4A-4C are illustrations of different embodiments of the distal end of endoscopes of the current disclosure.

DESCRIPTION OF THE EMBODIMENTS

Reference will now be made to exemplary embodiments of the invention, examples of which are illustrated in the accompanying drawings. Wherever possible, the same reference numbers will be used throughout the drawings to refer to the same or like parts.

The terms "proximal" and "distal" are used herein to refer to the relative positions of the exemplary endoscopic device 20. When used herein, "proximal" refers to a position relatively closer to the exterior of the body or closer to the surgeon using the endoscopic device 20. In contrast, "distal" refers to a position relatively further away from the surgeon using the endoscopic device 20 or closer to the interior of the body.

Figure 1:
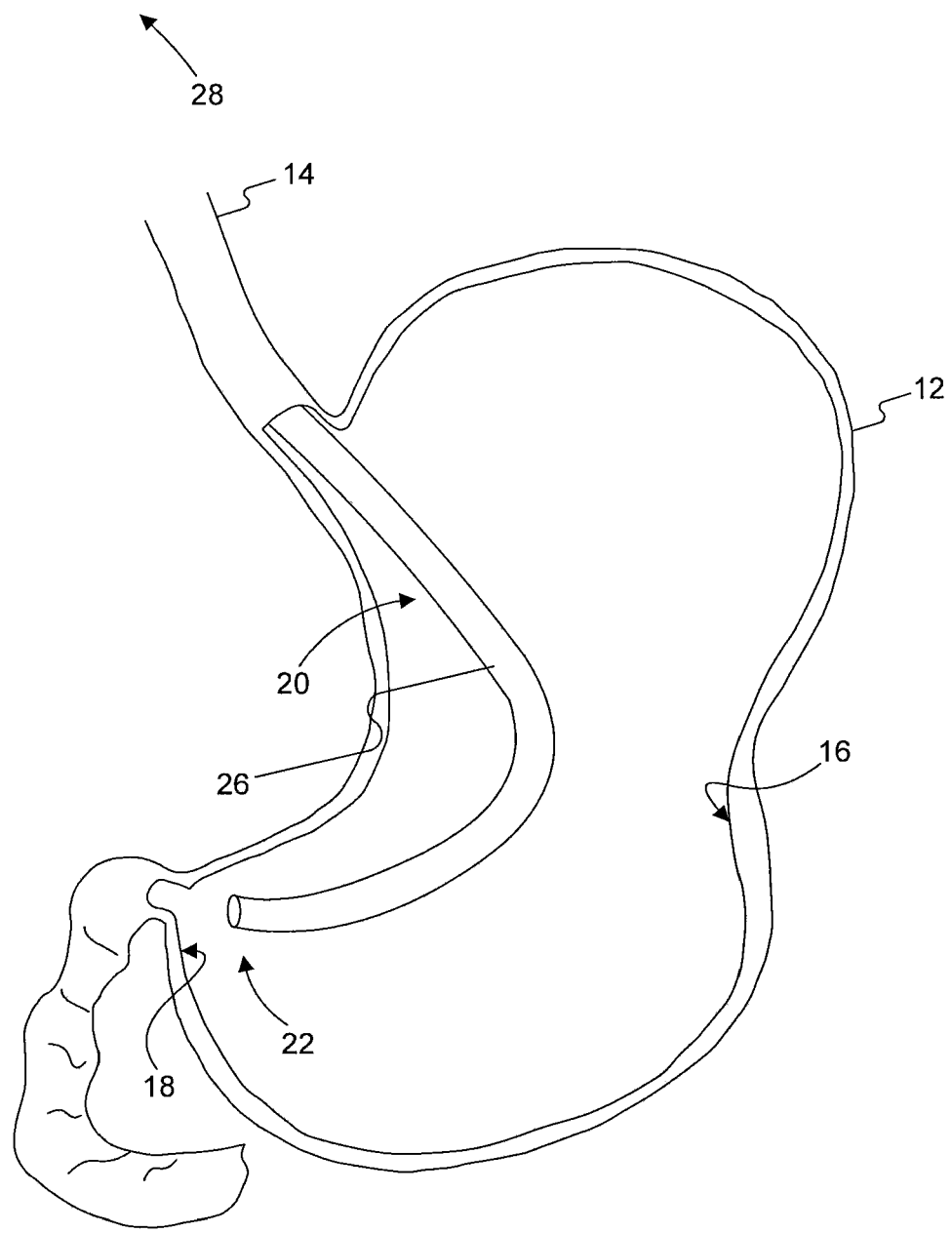
FIG. 1 is a schematic view of an embodiment of an endoscope performing an exemplary endoscopic procedure.

FIG. 1 depicts an exemplary endoscopic device 20 performing an exemplary medical procedure on a patient. Endoscopic device 20 may be inserted into stomach 12 through the esophagus 14, and positioned in stomach 12 such that a distal end 22 of endoscopic device 20 may be positioned proximate a work site 18 on stomach wall 16. A proximal end 28 (see FIG. 2B) of endoscopic device 20 may extend out of the body of the patient and may be controlled to perform the desired operations at the distal end 22 of the endoscopic device 20. It should be emphasized that the medical procedure illustrated in FIG. 1 is exemplary only, and that endoscopes of the current disclosure may be applied to any endoscopic application known in the art. It should also be emphasized that endoscopic device 20 of FIG. 1 can be any medical device that can be used to visualize a region inside the body from outside the body. For example, endoscopic device 20 of FIG. 1 may include any type of imaging endoscopes, guide tubes, catheters or the like without limitation.

Endoscopic device 20 may include a flexible elongate member 26 extending between the proximal end 28 and distal end 22. During use, distal end 22 may be positioned proximate work site 18 within a body and the proximal end 28 may be positioned outside the body. Elongate member 26 may be flexible so as to enable endoscopic device 20 to bend and pass through tortuous body passages as distal end 22 of endoscopic device 20 advances to work site 18. In some embodiments, elongate member 26 may be made of, or coated with, a polymeric or a lubricious material to enable the endoscopic device 20 to pass through body cavities with ease.

Figure 2A:
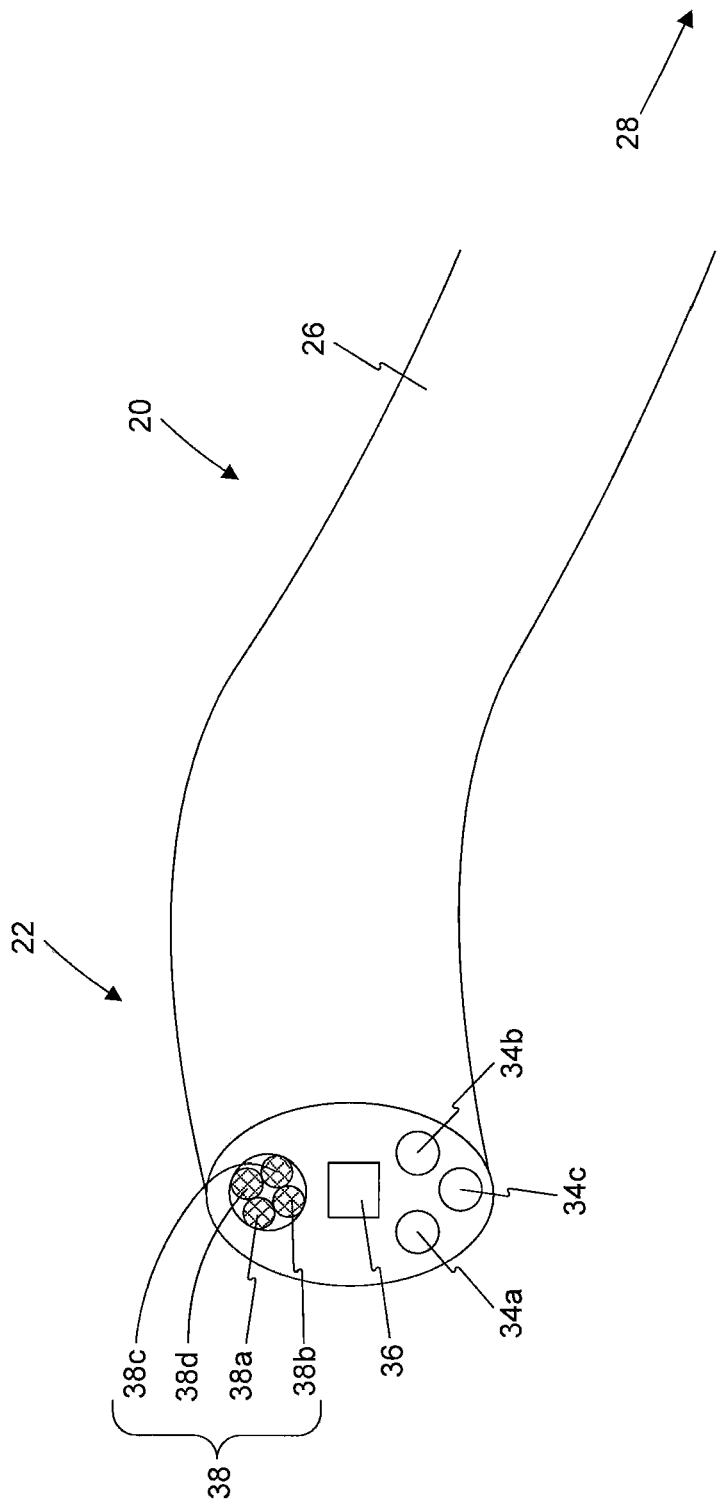
FIG. 2A is an illustration of the distal end of the endoscope of FIG. 1.
Figure 2B:
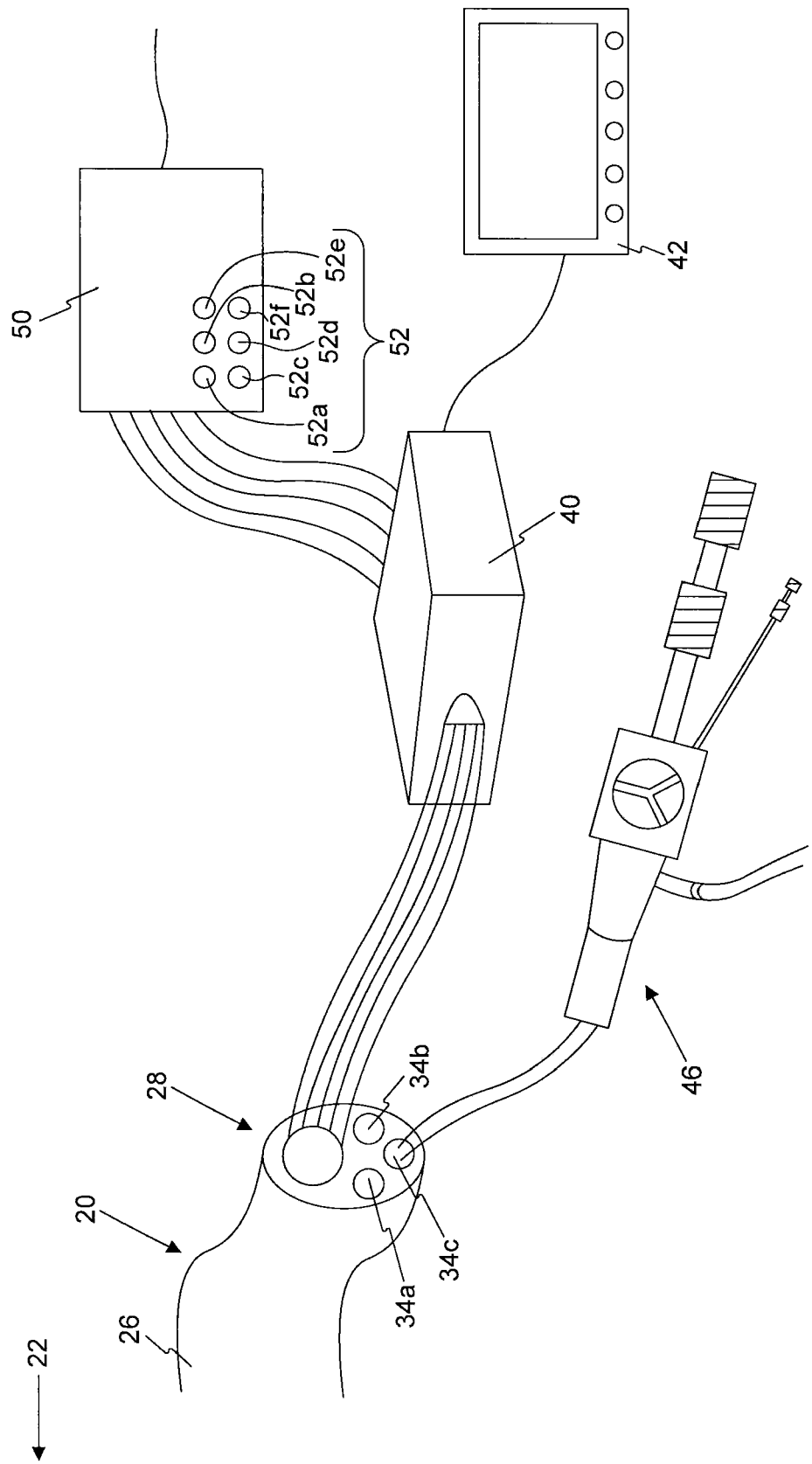
FIG. 2B is an illustration of the proximal end of the endoscope of FIG. 1.

FIGS. 2A and 2B are schematic illustrations of distal end 22 and proximal end 28, respectively, of endoscopic device 20. In the discussion that follows, reference will be made to both FIGS. 2A and 2B. Endoscopic device 20 may include one or more lumens 34a, 34b, 34c, etc. extending therethrough and terminating at distal end 22. These lumens may be configured to direct tools/instruments and the like to work site 18 from outside the body. Although these lumens are illustrated as being circular, in general, the lumens can have any cross-sectional shape. Distal end 22 of endoscopic device 20 may also include devices (36, 38) that are embedded or attached thereon. These devices may be configured to perform tasks to assist in the medical procedure at work site 18. Although not illustrated in FIG. 2A, distal end 22 of endoscopic device 20 may also include one or more end effectors that are configured to perform specific tasks at work site 18. These end effectors may be coupled to a distal end of an endoscopic device and may be operatively coupled to, and controlled by, an actuation device 46 (i.e. a handle) at the proximal end 28 of endoscopic device 20 (see FIG. 2B).

One or more of the lumens 34a, 34b, 34c may extend from distal end 22 to proximal end 28 longitudinally along elongate member 26. These lumens may have a constant cross-sectional shape along the entire length of elongate member 26 or may have a cross-sectional shape that changes along the length of elongate member 26. This change in cross-sectional shape along the length may be step wise or gradual. In some embodiments, some or all lumens may be lined with a polymeric or another layer or coating to facilitate use. The lumens 34a, 34b, 34c may provide access to instruments and facilities that may aid in performing desired medical procedures at work site 18. These lumens may include one or more of, among others, an irrigation lumen 34a, an aspiration lumen 34b, and a working lumen 34c.

The irrigation lumen 34a may be configured to facilitate fluid flow from proximal end 28 to distal end 22. In some embodiments, the irrigation lumen may be attached to a source of fluid at proximal end 28 and to a nozzle (or other similar device that is configured to alter fluid flow) at distal end 22. Aspiration lumen 34b may be configured to facilitate suction and/or fluid flow through it. In some embodiments, fluid may be directed from proximal end 28 to distal end 22 through irrigation lumen 34a to clean work site 18. Suction may then be applied at proximal end 28 of aspiration lumen 34b to remove the fluid (and/or biological material) from work site 18 through the aspiration lumen. In this manner, a tissue sample may be extracted out of the body through aspiration lumen 34b.

The working lumen 34c may include a conduit that is configured to deliver an endoscopic instrument or device to work site 18. The endoscopic instrument may include any tool that is configured to perform a desired function at work site 18 while being remotely controlled by actuation device 46 from outside the body. The endoscopic instrument may be configured as an end effector attached at the distal end of an endoscopic instrument. For instance, the endoscopic instrument may include surgical forceps attached at the distal end of links that may be manipulated from the proximal end by actuation device 46 to control the operation of the forceps at work site 18. In general, working lumen 34c may have any suitable shape, size, and configuration that is configured to pass the end effector therethrough. Although only one working lumen 34c is illustrated in FIG. 2A, in some embodiments, endoscopic device 20 may include multiple working lumens configured to direct a plurality of surgical tools to work site 18.

The devices on distal end 22 of endoscopic device 20 may include an imaging device 36 and an illumination device 38. Imaging device 36 may include a camera, imaging sensor (such as, for example, a complimentary metal-oxide semiconductor or a CMOS sensor), a light sensor, or another image receiving device (such as, for example, a fiber optic imaging device). Imaging device 36 may transmit an image signal to a monitor or other display device 42 positioned outside the body and viewable by the surgeon. The image signals may correspond to still pictures and/or transient images that display time varying images of work site 18 on the display device 42. In some embodiments, image sensor 36 may transmit the image signals to the display device 42 wirelessly, while in other embodiments imaging device 36 may transmit the signals using wire or a cable (fiber optic or another type of cable) embedded along the length of the elongate member 26. In some embodiments, image signals from imaging device 36 may be processed by a control device 40 before being directed to display device 42. It is also contemplated that, in some devices, control device 40 may also direct a control signal to imaging device 36 to control various aspects of its operation. In some embodiments, in addition to, or in place of imaging device 36 fixed to distal end 22, an imaging device may be delivered to distal end 22 through a working lumen of endoscopic device 20.

Illumination device 38 may include any device that is configured to illuminate work site 18. Illumination device 38 may include, among others, bulbs, LEDs, one or more fiber optic cables, and light guides. In one embodiment, the illumination device may include a plurality of fiber optic cables. Other embodiments may include a collection of one or more other types of light sources. In the embodiment illustrated in FIG. 2A, illumination device 38 is depicted as a cluster comprising four individual fiber optic cables 38a, 38b, 38c, and 38d. However, other embodiments may include a different number of fiber optic cables and a different positioning of the fiber optic cables (discussed with reference to FIGS. 4A-4C). These fiber optic cables 38a, 38b, 38c, and 38d may direct light to distal end 22 from an external light source at proximal end 28 to illuminate work site 18.

The external light source may include one or more LED, Xenon, or other light sources in an illumination control system 50. Illumination control system 50 may be configured to control and vary a characteristic of the light directed to each of the fiber optic cables individually. This characteristic may include intensity, wavelength, polarization, frequency, phase or any other characteristic that can vary the level of illumination directed through each of the individual fiber optic cables. That is, in one embodiment, illumination control system 50 may be configured to set the intensity of light directed to fiber optic cable 38a at a first level, the intensity of light directed to fiber optic cable 38b at a second level different from the first level, the intensity of light directed to fiber optic cable 38c at a third level different from the first and second levels, and the intensity of light directed to fiber optic cable 38d at a fourth level different from the first, second, and third levels.

Illumination control system 50 may also include one or more light sources, control electronics, and associated control algorithms that operate cooperatively to modulate the amount of light directed to each of the individual fiber optic cables 38a, 38b, 38c, and 38d. In one embodiment, illumination control system 50 may include a single light source with individual lenses, irises, and/or filters to modulate the amount of light directed to each of the individual fiber optic cables 38a, 38b, 38c, and 38d. Any optical arrangement known in the art may be used to split the light from the single light source into multiple beams having different characteristics and direct each beam through the individual fiber optic cables 38a, 38b, 38c, and 38d. In other embodiments, illumination control system 50 may include multiple light sources to vary the characteristic of light input to the individual fiber optic cables 38a, 38b, 38c, and 38d. In applications involving disposable endoscopes, illumination control system 50 may form the capital equipment that may be used along with a disposable endoscope. Since the illumination control system 50 may be reused with different disposable endoscopes, the sensitivity of cost of the illumination control system 50 to the application may be low.

Figure 3:
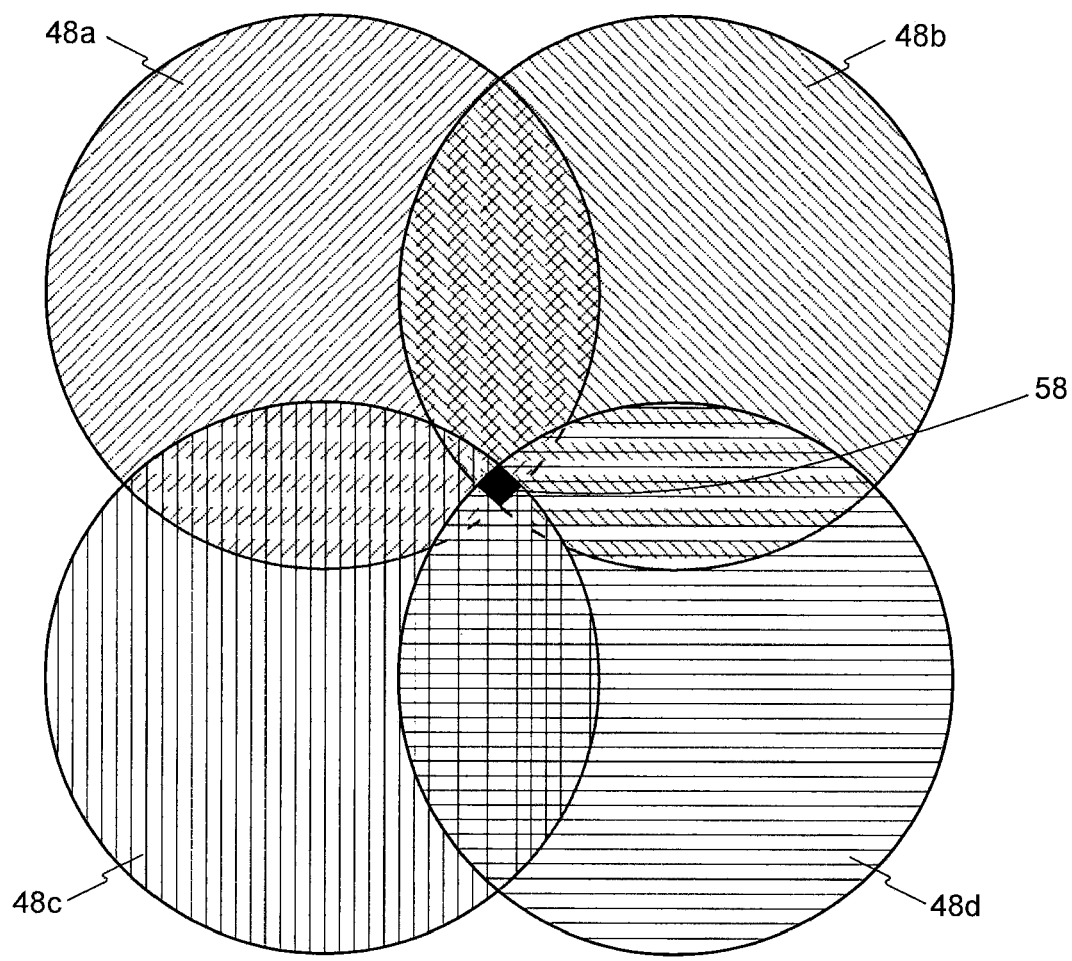
FIG. 3 is an illustration of illumination coverage at a work site using the endoscope of FIG. 1.

FIG. 3 illustrates an exemplary illumination coverage in work site 18 in an embodiment using four individual fiber optic cables. First region 48*a* may be the area illuminated by fiber optic cable 38*a*, second region 48*b* may be the area illuminated by fiber optic cable 38*b*, third region 48*c* may be the area illuminated by fiber optic cable 38*c*, and fourth region 48*d* may be the area illuminated by fiber optic cable 38*d*. The regions of overlap may be illuminated by multiple fiber optic cables and may naturally be areas of relatively high illumination. In some embodiments, distal end 22 of endoscopic device 20 may be manipulated to position an area of interest of work site 18 at a region of maximum overlap 58. Based on an image in display device 42, the surgeon may determine that some of the regions should be illuminated differently from other regions for good visualization of work site 18. Illumination control system 50 may include controls 52 (such as, for example, controls 52*a*-52*f*) to selectively vary the level of illumination in the different regions, including regions of overlap that are illuminated by multiple fiber optic cables. For instance, if an image in display device 42 indicates that the level of illumination in the first region 48*a* is too low and the level of illumination in the second region 48*b* is too high, the surgeon may manipulate the controls 52 of illumination control system 50 to increase the illumination level of first region 48*a* and decrease the illumination level of second region 48*b*.

In some embodiments, the endoscopic device 20 may include a plurality of preset illumination patterns. These preset illumination patterns may correspond to illumination patterns where the intensity (or another characteristic) of light through each fiber optic cable 38*a*-38*d* may be optimized for a certain application or for a certain location in the body. For example, one preset pattern may correspond to an illumination pattern that is optimized for a particular endoscopic procedure (such as, for example, hemostasis of a bleeding ulcer) and another preset pattern may correspond to an illumination pattern that is optimized for another endoscopic procedure or a particular location within the body (such as, for example, the esophagus). In some embodiments, some of the preset illumination patterns may be configured to change over time. For instance, an illumination pattern may change as the distal end 22 of the endoscopic device 20 traverses a body tract for optimal visibility of different sections of the body tract. These preset illumination patterns may be selected by a user, for example, by activating a control of illumination control system 50. The preset illumination patterns may be preset by a supplier or a user, and may be adapted to be modified as desired.

In some embodiments, illumination control system 50 may include a control algorithm to adjust the illumination of the work site automatically. This control algorithm may include software codes that analyze the image from imaging device 36 and automatically control the intensity of light in each of the fiber optic cables for optimal illumination of work site 18. For instance, analysis of a captured image from imaging device 36 may indicate that the first region 48*a* is relatively dark and the second region 48*b* is relatively bright as compared to the other regions. Illumination control system 50 may automatically vary the intensity of light directed to each of the individual fiber optic cables in steps until a subsequent image analysis indicates that the differences in illumination of different regions is within an acceptable threshold. In some embodiments, the illumination control system 50 may be configured to "learn" from each illumination adjustment operation and improve over time. In one such embodiment, the illumination control system 50 may include a self-learning neural network or another similar algorithm. The neural network may include a training mode and a usage mode. In the training mode, illumination control system 50 may be trained to output a selected pattern of light through each fiber optic cable for a particular image pattern on imaging device 36. In the usage mode, when this image pattern is detected in imaging device 36, the illumination control system 50 may output the selected pattern of light through the fiber optic cables. If an image pattern on imaging device 36 does not belong to a taught list of image patterns, a characteristic of light through each fiber optic cable may be manually or automatically adjusted for optimal illumination of work site 18, and the output pattern of light may be added to the taught list of image patterns.

FIGS. 4A through 4C illustrate the distal end 22 of different embodiments of endoscopic devices of the current disclosure. In endoscopic device 20A of FIG. 4A, four fiber optic cables 38*a*, 38*b*, 38*c*, and 38*d* are positioned at spaced locations on distal end 22. In endoscopic device 20B of FIG. 4B, six fiber optic cables 38*a*, 38*b*, 38*c*, 38*d*, 38*e*, and 38*f* are positioned at spaced locations on distal end 22. In endoscopic device 20C of FIG. 4C, four clusters of fiber optic cables, each cluster including four fiber optic cables, are positioned at spaced locations on distal end 22. The positioning of the fiber optic cables in FIGS. 4A-4C is only exemplary. In general, the fiber optic cables (38*a*, 38*b*, etc.) may be positioned at any location on distal end 22 of endoscopic device 20. In some embodiments, the fiber optic cables (38, 38*b*, etc.) may be positioned symmetrically about a center point of distal end 22 while in other embodiments they be positioned asymmetrically depending on the application, for example. In each of these embodiments, a characteristic of the light emitted by some or all of the individual fiber optic cables may be individually varied by illumination control system 50. For instance, in the embodiments of FIGS. 4A and 4B, the intensity of the light emitted by each of the individual fiber optic cables (38*a*, 38*b*, 38*c*, and 38*d* in the embodiment of FIG. 4A and 38*a*, 38*b*, 38*c*, 38*d*, 38*e*, and 38*f* in the embodiment of FIG. 4B) may be varied individually by illumination control system 50. And, in the embodiment of FIG. 4C, the intensity of light emitted by each cluster of fiber optic cables (38*a*-38*d*, 38*e*-38*h*, 38*i*-38*l*, and 38*m*-38*p*) may be varied individually.

Any type of fiber optic cable (plastic, glass, etc.) may be used as illumination device 38. Although in the description above, the intensity of light directed through each fiber optic cable is described as being varied, in general, any characteristic of light that can modulate the illumination at distal end 22 may be varied by illumination control system 50. For instance, in some embodiments, the characteristic of light that is varied by the illumination control system 50 may include a wavelength of the light directed through each fiber optic cable. Additionally, although illumination device 38 is described as being a fiber optic cable, this is not a limitation. In general, any illumination device that is capable of being individually controlled may be used as illumination device 38. For instance, in some embodiments, LEDs may be used as illumination device 38. In these embodiments, illumination control system 50 may control each LED individually to control a characteristic of the light emitted by each individual LED. In other embodiments, combinations of different illumination devices may be used.

In some embodiments, the illumination devices 38 at distal end 22 of endoscopic device 20 may be operatively coupled with one or more adjustable diffusing lenses or other adjustable lens membranes to selectively vary a characteristic of light emitted by each illumination device 38. In these embodiments, a characteristic of the light emitted by each illumination device 38 may be changed by selectively activating the diffusing lens or lens membrane associated with that illumination device. The diffusing lens or lens membrane may be selectively activated by any means, such as, for example, a pressure may be applied to the lens membrane to change its optical properties, and therefore, a characteristic of light passing through the membrane. A pressure may be applied to the lens membrane by applying an electric current to the membrane.

In some embodiments, the lenses may be independently controlled to aim light at or away from a particular point, direct, focus, obscure, and/or change a characteristic of (for example, frequency, etc.) of the light. In some embodiments, a lens or another optical member associated with an illumination device may be biased to provide more (or less) illumination to a region of work site 18 illuminated by that illumination device. In some embodiments, the illumination control system 50 may vary a cant or tilt of a fiber optic cable (or another illumination device) relative to a longitudinal axis of the endoscopic device 20 to vary a characteristic of light delivered to work site 18 through that cable. The cant of the fiber optic cable may be changed by advancing or retracting wedges or other positioning mechanisms associated with that cable. In some embodiments, combinations of light sources (such as, for example, LED and fiber optic) may be used to provide illumination. In some such embodiments, different combinations of these light sources may be used to vary the level of illumination directed at a particular region. In some embodiments, one or more light sensors could be used in addition to, or as, cameras. These light sensors may assist in automatically or manually adjusting the illumination effect.

The embodiments described herein are exemplary only, and it will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only, with a true scope of the invention being indicated by the following claims.

What is claimed is:

1. A medical device configured for insertion into a body, comprising:
    a member extending from a proximal end to a distal end and configured so that the distal end is positioned inside a stomach of the body while the proximal end is positioned outside the body, wherein the medical device is an endoscope having a handle at the proximal end that is accessible outside the body;
    an imaging device, a camera, a CMOS sensor, or a light sensor positioned at the distal end and configured to detect an image pattern;
    a plurality of light sources positioned at the distal end, wherein each light source illuminates a different region, and the regions together form the image pattern; and
    a control device having a processor configured to execute instructions that automatically control each light source of the plurality of light sources by varying a first characteristic of light directed through a first light source of the plurality of light sources independent of a second characteristic of light directed through a second light source of the plurality of light sources based on the detected image pattern,
    wherein the control device also is configured to:
    compare the detected image pattern to a plurality of image patterns;
    automatically adjust a characteristic of each light source to at least one of a plurality of preset illumination patterns based on the detected image pattern, if the detected image pattern corresponds to at least one of the plurality of image patterns; and
    automatically control each light source of the plurality of light sources to deliver light according to the at least one of the plurality of preset illumination patterns, wherein each preset illumination pattern of the plurality of preset illumination patterns is optimized for a different endoscopic procedure or a different location within the body.

2. The medical device of claim 1, wherein the plurality of light sources includes at least one of a plurality of fiber optic cables that terminate at the distal end and at least one LED.

3. The medical device of claim 1, wherein each light source of the plurality of light sources is positioned at a different location at the distal end.

4. The medical device of claim 1, wherein the first characteristic of light delivered through the first light source includes at least one of an intensity, a wavelength, a polarization, a frequency, or a phase of light.

5. The medical device of claim 1, further including one or more adjustable lenses configured to vary the first characteristic of light directed through the first light source.

6. The medical device of claim 5, wherein the one or more adjustable lenses are configured to be adjusted by a change in pressure applied to the one or more adjustable lenses.

7. The medical device of claim 6, wherein the change in pressure applied to the one or more adjustable lenses is achieved by an electric current applied to the one or more adjustable lenses.

8. The medical device of claim 1
    wherein the control device also is configured to:
    receive a manual adjustment of a characteristic of one or more of the plurality of light sources or automatically adjust a characteristic of one or more of the plurality of light sources to create a new illumination pattern for the detected image pattern, if the detected image pattern does not correspond to at least one of the plurality of image patterns; and
    add the new illumination pattern to the plurality of image patterns if the detected image pattern does not correspond to at least one of the plurality of image patterns.

9. The medical device of claim 8, wherein each preset illumination pattern includes a different characteristic of light for at least one of the plurality of light sources than any other preset illumination pattern.

10. The medical device of claim 9, wherein the different characteristic of light includes at least one of an intensity, a wavelength, a polarization, a frequency, or a phase of light.

11. The medical device of claim 1, wherein the control device is configured to automatically change the preset illumination pattern as the plurality of light sources traverse through different sections of the body.

12. The medical device of claim 1, wherein each preset illumination pattern includes a different characteristic of light for at least one of the plurality of light sources than any other preset illumination pattern.

13. The medical device of claim 12, wherein the different characteristic of light includes at least one of an intensity, a wavelength, a polarization, a frequency, or a phase of light.

14. The medical device of claim 1, wherein the control device is configured to change the preset illumination pattern as a function of time.

15. The medical device of claim 1, wherein the control device is configured to process adjustments to a given preset illumination pattern and automatically output an adjusted preset illumination pattern based on detection of the image pattern.

16. The medical device of claim 1, wherein the medical device includes the imaging device, and wherein the imaging device includes a fiber optic imaging device.

* * * * *